United States Patent [19]
Yokoyama et al.

[11] Patent Number: 5,041,660
[45] Date of Patent: Aug. 20, 1991

[54] NOVEL ALPHA-CHLOROKETONE DERIVATIVE AND PROCESS FOR PREPARATION THEREOF

[75] Inventors: Keiichi Yokoyama, Iwakuni; Yoshio Noguchi, Waki; Noriaki Kihara, Iwakuni, all of Japan

[73] Assignee: Mitsui Petrochemical Industries, Ltd., Tokyo, Japan

[21] Appl. No.: 602,391

[22] Filed: Oct. 24, 1990

Related U.S. Application Data

[63] Continuation of Ser. No. 117,572, Nov. 6, 1987, abandoned.

[30] Foreign Application Priority Data

Nov. 7, 1986 [JP] Japan ................. 61-263958

[51] Int. Cl.$^5$ .................. C07C 323/41; C07C 323/42
[52] U.S. Cl. .................... 564/215; 564/186; 548/342
[58] Field of Search ................. 564/186, 215; 548/342

[56] References Cited

U.S. PATENT DOCUMENTS 4,814,500  3/1989  Kihara et al. ................. 548/342 X

FOREIGN PATENT DOCUMENTS

| 21637 | 1/1981 | European Pat. Off. . |
| 36684 | 9/1981 | European Pat. Off. . |
| 46635 | 7/1985 | European Pat. Off. . |
| 267055 | 5/1988 | European Pat. Off. ............ 564/215 |
| 63-60970 | 3/1988 | Japan . |
| 60971 | 3/1988 | Japan .................. 548/342 |
| 79877 | 4/1988 | Japan .................. 548/342 |

OTHER PUBLICATIONS

Wegner et al., Arch. Pharm., 310, 380-385 (1977).
Chemical Abstracts, 97:2687f (1982).

*Primary Examiner*—Carolyn S. Elmore
*Attorney, Agent, or Firm*—Sherman and Shalloway

[57] ABSTRACT

Disclosed is a novel α-chloroketone derivative as a synthesis intermediate of N-cyano-N'-methyl-N''-(2-((5-methyl-1H-imidazol-4-yl)methylthio)ethyl)guanidine (general name: Cimetidine) which shows an action of controlling the secretion of gastric acid and is valuable as a medicine for remedy of a gastric ulcer. This α-chloroketone derivative is prepared by reacting disulfide derivative with sulfuryl chloride and reacting the reaction product with methylvinyl ketone or by reacting a mercapto derivative with 3-chloro-3-buten-2-one.

2 Claims, No Drawings

NOVEL ALPHA-CHLOROKETONE DERIVATIVE AND PROCESS FOR PREPARATION THEREOF

This application is a continuation, of application Ser. No. 07/117,572 filed Nov. 6, 1987 now abandoned.

BACKGROUND OF THE INVENTION (1) Field of the Invention

The present invention relates to a novel α-chloroketone derivative valuable as a synthesis intermediate leading to Cimetidine having an action of controlling the secretion of gastric acid an being excellent as a medicine for remedy of a gastric ulcer.

(2) Description of the Related Art

As the process for synthesizing Cimetidine, there is known, for example, a process disclosed in Japanese Patent Publication No. 24422/78, which is represented by the following reaction formula:

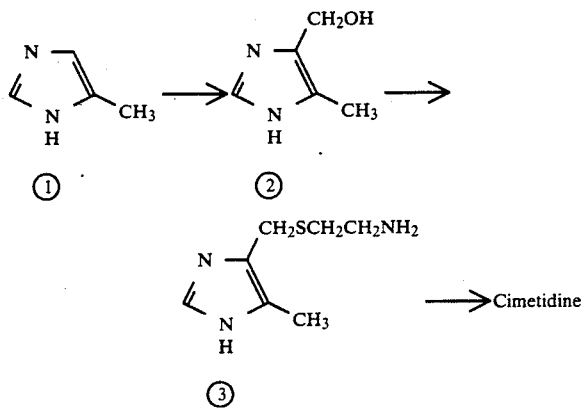

Namely, in many cases, the starting compound having an imidazole ring is used and necessary substituents are introduced into this starting compounds, and the compound ③ is often an important intermediate.

However, in this process, the starting imidazole derivative is expensive and since the reaction is a multi-staged reaction, the manufacturing cost is high. Therefore, the process is not advantageous from the industrial viewpoint.

SUMMARY OF THE INVENTION

We made research with a view to developing a process for synthesizing Cimetidine without using an expensive imidazole derivative as the starting compound.

As the result, we developed a process in which a compound represented by the following formula (I) is synthesized by reacting a compound ④ with a compound ⑤ or by reacting a compound ⑥ with a compound ⑦, this compound (I) is reacted with an organic acid ammonium compound such as $HCOONH_4$ and an ortho-formic acid ester, published as Japanese Patent Application Laid-Open Specification No. 60970/88, discloses a method for preparation of an imidazole derivative represented by the following formula (II).

The starting material (I) in the reaction formula (1) can be easily synthesized by a method described in the patent application by the same applicant of the same filing data as of this application. As the organic acid ammonium ($R-COONH_4$), it is possible to use an ammonium salt of aliphatic carboxylic acid, such as ammonium formate, ammonium acetate and ammonium propionate, or an ammonium salt of aromatic carboxylic acid, such as ammonium benzoate, ammonium p-toluate and ammonium naphthoate. While, as the formic acid derivative used in the reaction, it is possible to use orthoformate, such as methyl orthoformate and ethyl orthoformate, or formate, such as ethyl formate, propyl formate and phenyl formate. Moreover, this reaction can be carried out either in the non-solvent state or in a solvent. Examples of the solvent include aliphatic alcohol, such as methanol, ethanol, propanol and isopropanol, aromatic hydrocarbon, such as benzene, toluene and xylene, ether, such as diethyl ether, tetrahydrofuran and dioxane, nitrile, such as acetonitrile and propionitrile, halogenated hydrocarbon, such as dichloromethane, chloroform, tetrachloromethane and dichloroethane, aliphatic carboxylic acid, such as formic acid and acetic acid, heterocyclic aromatic compound, such as pyridine and picoline, and amide, such as formamide and dimethylformamide.

An amount of the organic acid ammonium to the compound (I) is 1 to 50 moles, preferably 2 to 10 moles. Similarly, an amount of the formic acid derivative is 1 to 50 moles, preferably 2 to 10 moles. Moreover, an amount of the solvent to the organic acid is 2 to 50 times by weight, preferably 5 to 30 times by weight. The reaction temperature is 20 to 200° C., preferably 60 to 150° C., and the reaction time is 10 minutes to 5 hours, preferably 30 minutes to 3 hours. After completion of the reaction, a Cymethydine-like compound (II) can be obtained by usual separation and purification, as explained by the following examples:

Example 1

3.15g (50 mmole) of ammonium formate and 5.30g (50 mmole) of methyl orthoformate were added to solution which was obtained by dissolving 1.31g (5 mmole) of N-cyano-N'-methyl-N''-[2-(2-bromo-3-oxobutylthio)ethyl]guanidine in 25 ml of formamide. Then, the mixture was stirred for 2 hours at 80° C. After completion of the reaction, the solvent was removed by distillation under vacuum. Thereafter, a part of the residue was analyzed by high-performance liquid chromatography (Column: ZORBAX-ODS (Dupont), Solvent: Water/MeoH/ACOH/$Et_3N$=700/300/0.6/0.6). The yield was 27%. The remainder of the residue was purified by silica-gel column chromatography (Developing Solvent: MeOH/$CH_2Cl_2$=1/10). As a result, 0.23g (Yield: 18.5%) of Cymethydine was obtained as white crystal powder. The product had a melting point of 139 to 141° C., and showed an IR spectrum and $^1$H-NMR spectrum inherent to standard Cymethydine.

Example 2

Cymethydine was prepared in the same manner as in Example 1 except that 6.3g (100 mmole) of ammonium formate and 10.6g (100 mmole) of methyl orthoformate were used, and the reaction was carried out in the non-solvent state. The yield of Cymethydine was 12.2% (HPLC).

Examples 3-6

Cymethydine was prepared in the same manner as in Example 1 except that the solvent was changed variously as shown in the following table. Compound (I) is reacted with formamidine (Arch. Pharm., 310, 380 (1977) discloses the synthesis of 60-substituted 4(5)-methoxymethyl(5)4-methyl-imidazole. As stated therein since nucleasubstituted 4(5)-hydroxymethyl-imidazole could be advantageously prepared from iminoesters and dihydroxy-acetone in accordance with developed methods (2,3), we expect that α-substituted analogues may be prepared from the corresponding α,β-dihydroxy ketones, which in turn may be obtained from α,β-unsaturated ketones through hydroxylation in the presence of osmium tetraoxide.

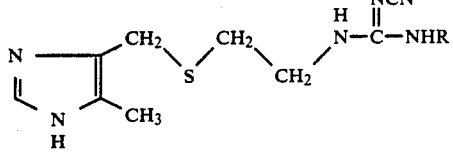

(wherein R is a lower alkyl group) by reaction of a cyanoguanidine derivative represented by the following formula (I):

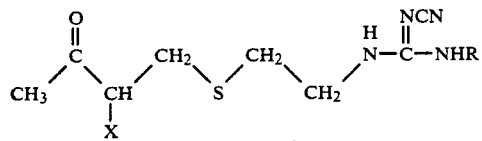

(wherein X is chlorine or bromine, and R is a lower alkyl group) with organic acid ammonium and a formic acid derivative.

As shown by a reaction formula (1), an objective compound like Cymethydine represented by the formula (II) can be prepared by reaction of a cyanoguanidine derivative (I) in the presence of organic acid ammonium and a formic acid derivative such as orthoformate or formate.

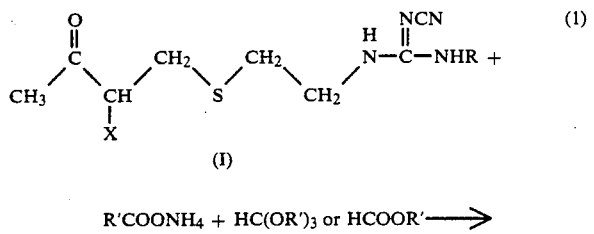

R'COONH$_4$ + HC(OR')$_3$ or HCOOR' ⟶

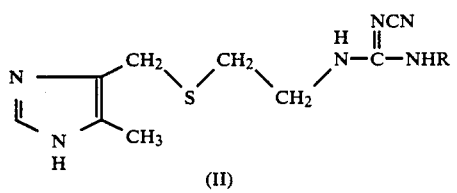

| Example No. | Solvent | Yield (%) (HPLC) |
|---|---|---|
| 3 | EtOH | 12.6 |
| 4 | i-PrOH | 18.3 |
| 5 | CH$_3$CN | 12.4 |
| 6 | DMF | 9.8 |

Examples 7-10

Cymethydine was prepared in the same manner as in Example 1 except that DMF was used in place of formamide, and methyl orthoformate was changed into various formic acid derivatives as shown in the following table.

| Example No. | Formic Acid Derivative | Yield (%) (HPLC) |
|---|---|---|
| 7 | HC(OEt)$_3$ | 8.4 |
| 8 | HCOOMe | 6.0 |
| 9 | HCOOEt | 8.0 |
| 10 | HCOOH | 17.4 |

The so-produced cymethydine (N-cyano-N'-methyl-N''-{2-(5-methyl-4-imidazolylmethylthio)ethylguanidine) is used for controlling secretion of acid in the stomach based on histamine H$_2$-receptor antagonism.)

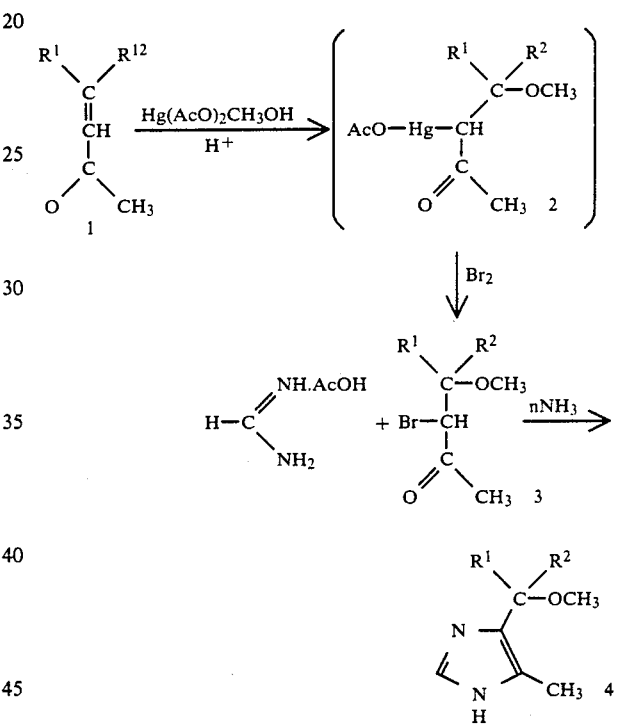

If required, the respective carbinoles may be prepared from 4 by ethereal cleavage with HI. The synthesis of thioethers, if desired, may preferably be started directly from the compound 4. If the formamidine acetate is replaced with substituted amidine or imino ester, then C-2 substituted imidazole 4 is obtained. In examination of the compound 3 converted in formamide according to Bredereck (7), only a small amount of the compound 4 could be detected.

The structure of the imidazole-ether 4 was determined by the $^{13}$C—NMR spectroscopy. The shift data, as given in Table 2, were taken from the broad band-decoupled spectra. Correlation is based on the known data from literatures for substituted imidazoles (8) as well as for alkyl- and alkoxyl-structures (9). Further, referring to the off- or gated-decoupled spectra, a degree of substitution for each C-atom was determined.

TABLE 1

Represented 4

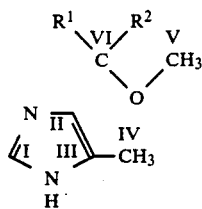

| 4 | R¹ | R² |
|---|---|---|
| a | H | H |
| b | VII<br>CH₃ | H |
| c | VII VIII<br>CH₂—CH₃ | H |
| d | VII VIII IX<br>CH₃—CH₂—CH₃ | H |
| e | VII VIII IX<br>CH—(CH₃)₂ | H |
| f | VII⌬X (VIII, IX) | H |
| g | VII<br>CH₃ | VII<br>CH₃ |

TABLE 2

$^{13}$C-chemical shift of 4 ($\delta$-value in ppm, relative to TMS = 0). Solvent CDCl₃-15%; Quaternary C-atom in brackets.

| 4 | I | II | III | IV | V | VI | VII | VIII | IX | X |
|---|---|---|---|---|---|---|---|---|---|---|
| a | 133.8 | (129.6) | (128.3) | 9.9 | 57.4 | 65.8 | | | | |
| b | 134.2 | (132.8) | (127.4) | 10.5 | 55.7 | 71.7 | 21.3 | | | |
| c | 134.2 | (131.1) | (128.7) | 10.6 | 55.9 | 77.6 | 28.5 | 10.3 | | |
| d | 134.3 | (131.1) | (128.8) | 10.8 | 55.9 | 75.9 | 37.8 | 19.2 | 14.0 | |
| e | 134.2 | (130.2) | (129.6) | 11.2 | 56.5 | 82.1 | 33.9 | 19.0 | 19.7 | |
| f | 133.7 | (131.8) | (127.1) | 10.2 | 56.3 | 78.1 | (141.0) | 126.5 | 128.0 | 127.1 |
| g | 132.5 | (135.3) | (126.2) | 11.9 | 50.2 | (75.0) | 27.1 | | | |

The methyl groups IV and VIII of 4c could not be clearly classified due to their slight shift difference of 0.3 ppm. For 4e, the both methyls VIII and IX of isopropyl groups show two separate signals with a shift difference of 0.7 ppm. The detailed description of this effect will be an object of the later study.

For the sure classification of signals generated from imidazole and phenyl portions of 4f, the known data for enzylalcohol[9] as well as for the results shown in Table 3 of 4(5)-benzyl-imidazole were taken into consideration.

TABLE 3

$^{13}$C-chemical shift of 4(5)-benzyl-imidazole and 2,5(4)-diethyl-4(5)-benzyl-imidazole (appatives; vgl Jab. 2)

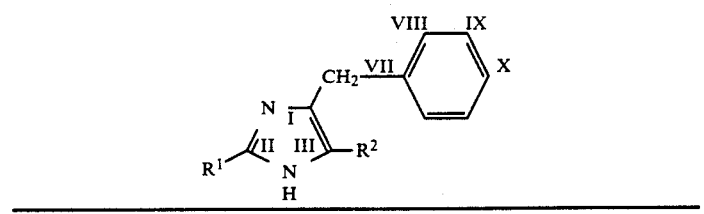

| R¹=R² | I | II | III | VII | VIII | IX | X |
|---|---|---|---|---|---|---|---|
| H | 135.1 | (136.8) | 117.9 | (140.0) | 128.8 | 128.8 | 126.6 |
| C₂H₅ | (148.2) | (132.6) | (128.5) | (141.0) | 128.3 | 128.3 | 125.9 |

| 3 | Substance | Yield % d.Th. | Sdp.°/Torr | Formula (Mol. Wt.)(ms) |
|---|---|---|---|---|
| a. | 3-bromo-4-methoxy-2-butanone | 55 | 71–74/12 | C₅H₉BrO₂ (181) |
| b. | 3-bromo-4-methoxy-2-pentanone | 65 | 77/15 | C₆H₁₁BrO₂ (195) |
| c. | 3-bromo-4-methoxy-2-hexanone | 40 | 45–50/0.4 | C₇H₁₃BrO₂ (209) |
| d. | 3-bromo-4-methoxy-2-heptanone | 48 | 63–66/1.5 | C₈H₁₅BrO₂ (223) |
| e. | 3-bromo-4-methoxy-5-methyl-2-hexanone | 38 | 52–58/0.4 | C₈H₁₅BrO₂ (223) |

TABLE 3-continued $^{13}C$-chemical shift of 4(5)-benzyl-imidazole
and 2,5(4)-diethyl-4(5)-benzyl-imidazole
(appatives; vgl Jab. 2)

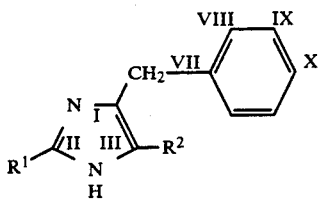

| | | | | |
|---|---|---|---|---|
| f. | 3-bromo-4-methoxy-4-phenyl-2-butanone[6] | 51 | 101/0.6 | $C_{11}H_{13}BrO_2$ (257) |
| g. | 3-bromo-4-methoxy-4-methyl-2-pentanone[11] | 64 | 88–90/15 | $C_7H_{13}BrO_2$ (209) |

The dc examination of the reaction mixture has shown a high conversion rate, but the isolation of hydroscopic substances has been found difficult.

This problem may be avoided by preparing lipophilic methoxy analogues 4, which may be isolated by extraction with chloroform from the mixture. For synthesis of 4, α-hydroxy ketones [2,3] as well as α-halogenoketones [4] were taken into consideration. Among them, α-bromo-β-methoxy-ketone[3], which may be prepared from 1 through the methoxymercurization[5,6] and subsequent demercurization, is found very suitable. The α-acetoxymercuric-β-methoxy ketones 2 formed as intermediates must not be isolated, but may be subjected directly to the demercurization with bromine. The desired α-substituted 4(5)-methoxy-methyl-5(4)-methylimidazoles 4 are obtained in a good or very good yield by reacting the compound 3 with formamidine acetate or formimino ethyl ester HCl in liquid ammonia for 5~15 hrs. at 30~50° C. under the pressure of 12~18 at.

Experimental Part

Melting point (uncorrected): Apparatus for determination of melting point according to Dr. Tottori. Elemental analysis: Microanalytical laboratory in Johannes Gutenberg University Mainz. Mass-spectroscopy: Type MATCH7A. $^{13}C$—NMR spectroscopy: Bruker WH-90 spectrometer (8K/4K). Running numbers amount to each 5000 scans at 1.47 Hz/address corresponding to a residence time of 83 sec.

General Instructions for Preparation of 3

The compound 1 used as starting materials were commercially available or prepared through Aldol-addition followed by hydrolysis with iodine[10].

To a suspension of 1M mercury-II acetate in 1.5 l of methanol were added twenty drops of 60% perchloric acid and 1 mol of the compound 1. After stirring at room temperature for 0.5 hrs., 1 mole of bromine was added dropwise within 1 hour., and then excessive methanol was evaporated. The residue was digested three times each with 500 ml of ether, and the ether solution was shaken with aqueous sodium bromide solution, dried, concentrated and distilled.

| | | | | | Analysis calculated: found: | | |
|---|---|---|---|---|---|---|---|
| 4 | Substance | Yield % d. Th. | Melting point °C. | Formula (Mol. Wt.) | c | H | N |
| a. | 4(5)-Methoxymethyl-5(4)-methyl-imidazole | 86 | 74 | $C_6H_{20}N_2O$ (126.2) | 57.12 56.80 | 7.99 7.69 | 22.21 22.49 |
| b. | 4(5)-(1-Methoxyethyl)-5(4)-methyl-imidazole | 80 | 113 | $C_7H_{12}N_2O$ (140.2) | 59.98 60.12 | 8.63 8.74 | 19.98 19.77 |
| c. | 4(5)-(1-Methoxypropyl)-5(4)-methyl-imidazole | 45 | 65 | $C_8H_{14}N_2O$ (154.2) | 62.31 62.36 | 9.15 8.94 | 18.17 18.54 |
| d. | 4(5)-(1-Methoxybutyl)-5(4)-methyl-imidazole | 62 | 82 | $C_9H_{16}N_2O$ (168.2) | 64.25 64.09 | 9.59 9.65 | 16.65 17.01 |
| e. | 4(5)-(1-Methyoxy-2-methyl-propyl)-5(4)-methyl-imiazole | 53 | 107 | $C_9H_{16}N_2O$ (168.2) | 64.25 64.54 | 9.59 9.55 | 16.65 16.52 |
| f. | 4(5)-( -Methoxybenzyl)-5(4)-methyl-imidazole | 75 | 110 | $C_{12}H_{14}N_2O$ (202.3) | 71.26 70.97 | 6.98 7.12 | 13.85 14.00 |
| g. | 4(5)-(1-Methoxy-1-methyl-ethyl-5(4)-methyl-imidazole | 66 | 151 | $C_8H_{14}N_2O$ (154.2) | 62.31 62.66 | 9.15 9.28 | 18.17 18.14 |

General Instruction for preparation of 4

0.2 Mole of the compound 3 and 0.22 mole of formamidin acetate were introduced into 250 ml of liquid ammonia, and reacted in an autoclave for 5~15 hrs. at 30~50° C. under the pressure of 12~18 at. After evaporation of ammonia, a pale yellow oily residue was mixed with water, the compound 4 was isolated by a plural times of extraction with chloroform, and then the chloroform phase was dried and evaporated. The remaining pale yellow oil was crystallized during trituration with a small quantity of ether.

Notes:

2. P. Dziuron and W. Schunack, Arch. Pharm. (Weinhein) 306,347 (1973)

3. P. Dziuron and W. Schunack, Arch. Pharm. (Weinhein) 307,470 (1974)

4. K. Wegner and W. Schunack, Arch. Pharm. (Weinhein) 307,972 (1974)

5. A. J. Bloodworth and R. J. Bunce, J. Chem., Soc. C 1971,1453

6. R. G. Smith, H.E. Ensley and H. E. Smith, J. Org. Chem. 37, 4430 (1972)

7. H .Bredereck, Angew. Chem. 71, 760 (1959)

8. H. J. Sattler, V. Stoeck and W. Schunack, Arch. Pharm. (Weinhein) 308, 795 (1975)

9. J. T. Clerc, E. Pretsch and S. Sternhell. $^{13}$CNuclear-Magnetic Resonance Spectroscopy, P. 44, 62, 101 Akodemische Verlaggesellschaft, Frankfurt/M, 1973

10. A. T. Nielsen and W. J. Houlikan, Org. React. 16, 1 (1968)

11. V. Calo, L. Lopez, G. Pecse and P. E. Todesco, Tetrahedron 29, 1625 (1973).), and the resulting compound (8) is hydrolyzed according to customary procedures to obtain the above-mentioned important intermediate (3).

wherein R is as defined above, with surfuryl chloride and reacting the resulting reaction product with methylvinyl ketone.

In accordance with still another aspect of the present invention, there is provided a process for the preparation of an α-chloroketone derivative represented by the above-mentioned general formula (I) (wherein R stands for a hydrogen atom, a lower alkyl group having 1 to 4 carbon atoms or an aryl group), which comprises reacting a mercapto derivative represented by the following general formula (III):

$$HSCH_2CH_2NH\overset{O}{\overset{\|}{C}}-R \qquad (III)$$

wherein R is as defined above, with 3-chloro-3-buten-2-one.

DETAILED DESCRIPTION OF THE PREFERRED EMBODIMENTS

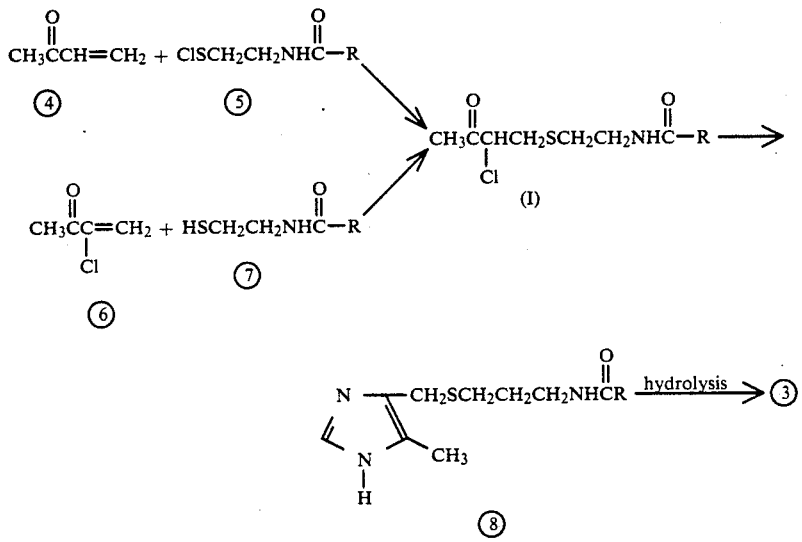

More specifically, in accordance with the present invention there is provided an α-chloroketone derivative as a synthesis intermediate of Cimetidine, which is represented by the following general formula (1):

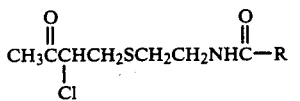

wherein R stands for a hydrogen atom, a lower alkyl group having 1 to 4 carbon atoms or an aryl group.

In accordance with another aspect of the present invention, there is provided a process for the preparation of an α-chloroketone compound represented by the above-mentioned general formula (I) (wherein R stands for a hydrogen atom, a lower alkyl group having 1 to 4 carbon atoms or an aryl group), which comprises reacting a disulfide derivative represented by the following general formula (II):

The α-chloroketone derivative is represented by the above-mentioned general formula (I).

In this general formula, R stands for a hydrogen atom, a lower alkyl group having 1 to 4 carbon atoms or an aryl group. As the lower alkyl group having 1 to 4 carbon atoms, there can be mentioned, for example, a methyl group, an ethyl group, an n-propyl group, an isopropyl group, an n-butyl group, an isobutyl group and a sec-butyl group. A hydrogen atom and a methyl group are especially preferred as the substituent R. AS the aryl group, there can be mentioned a phenyl group and a phenyl group substituted with a lower alkyl group. Compounds illustrated in the examples given hereinafter are preferred as the compound of the present invention.

The compound of the present invention represented by the general formula (I) can be prepared through the above-mentioned two routes (processes A and B):

(Process A)

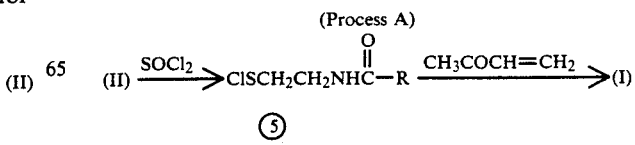

-continued
(Process B)

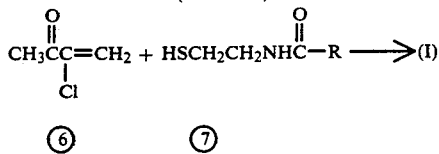

(Process A)

When the compound represented by the following formula (II) is mixed with sulfuryl chloride, a reactive intermediate ⑤ is formed. If methylvinyl ketone is added to the reaction mixture without isolation of the compound ⑤, the compound of the present invention represented by the general formula (I) is synthesized. More specifically, the compound ⑤ is synthesized by mixing the compound of the formula (II) with sulfuryl chloride in an amount of 1 to 2 moles, preferably 1 to 1.2 moles, per mole of the compound of the general formula (II) in a non-protonic polar solvent such as DMF, DMSO, acetone or N-methylpyrrolidone or a halogen type solvent such as chloroform, dichloromethane or 1,2-dichloroethane, preferably in DMF or chloroform as the solvent, at a temperature of −60 to 50° C., preferably −40 to 30° C. The compound of the present invention represented by the general formula (I) is synthesized by adding methylvinyl ketone in an amount of 1 to 10 moles, preferably 1 to 3 mole, per mole of the compound of the formula (II) to the obtained reaction liquid at a temperature of −60 to 50° C., preferably −40 to 30° C. After the reaction, the intended compound can be obtained by a customary post treatment.

(Process B)

The compound of the present invention is synthesized by dissolving the compound ⑥ in an inert solvent to form a solution and adding the compound ⑦ to the solution. As the reaction solvent, there can be used alcohol type solvents, halogenated hydrocarbon type solvents, ester type solvents, ether type solvents and non-protonic polar solvents. As the alcohol type solvent, there can be mentioned, for example, methanol, ethanol, n-propanol, isopropanol and n-butanol. As the halogenated hydrocarbon solvent, there can be mentioned, for example, chloroform, dichloromethane and 1,2-dichloroethane. As the ester type solvent, there can be mentioned, for example, methyl acetate, ethyl acetate and butylacetate. As the ether type solvent, there can be mentioned, for example, dimethyl ether, diethyl ether, dipropyl ether and dibutyl ether. As the non-protonic polar solvent, there can be mentioned acetone, DMF, MMSO, N-methylpyrrolidone and acetonitrile. Of these solvents, methanol, ethanol, chloroform, dichloromethane and ethyl acetate are preferred.

The reaction temperature is −40 to 30° C., preferably −20 to 10° C. The molar ratio of the compounds ⑥ and ⑦ is from 2/1 to 1/2, preferably 1/1. After the reaction, the intended compound can be obtained by a customary treatment.

The present invention will now be described in detail with reference to the following examples and referential examples that by no means limit the scope of the invention.

Referential Example 1

Synthesis of N,N′-diformylcysteamine

A mixture of 45.0 g (200 millimoles) of cysteamine dihydrochloride, 44.8 g (400 millimoles) of potassium t-butoxide, 150 mλ of methyl formate and 400 mλ of methanol was refluxed for 5 hours and the solvent was removed by distillation under reduced pressure. The residue was purified by the silica gel column chromatography (developed with methanol/ethyl acetate (1/10)) to obtain 37.0 g of intended N,N′-diformylcysteamine in the form of an oily product (the yield was 88%).

$H^1$-NMR Spectrum (DMSO-$d_6$, δ ppm): 2.74–2.90 (6H, m), 3.29–3.51 (6H, m), 8.06 (2H, s), 8.20 (2H, brs)

Example 1

Synthesis of
8-amino-3-chloro-N-formyl-5-thiaheptan-2-one
(process A)

In 10 mλ of DMF was dissolved 1.04 g(5.0 millimoles) of N,N′-diformylcysteamine, and 0.67 g (5.0 millimoles) of sulfuryl chloride was added dropwise to the solution at −40° C. After the mixture was stirred for 30 minutes, 0.93 g (13 millimoles) of methylvinyl ketone was added dropwise and the mixture was stirred for 30 minutes. The reaction mixture was neutralized with an aqueous solution of sodium hydrogencarbonate and extracted with chloroform. Chloroform was removed by distillation under reduced pressure and the residue was purified by the silica gel column chromatography developed with ethyl acetate/hexane (3/1)) to obtain 0.35 g of intended 8-amino-3-chloro-N-formyl-5-thiaheptan-2-one in the form of an oily product (the yield was 33%).

$H^1$-NMR Spectrum (DMSO-$D_6$, δ ppm): 2.39 (3H, s), 2.76 (2H, t, J=7 Hz), 2.89–3.20 (2H, m), 5.20 (2H, q, J=7 Hz), 4.36 (1H, dd, J=7 Hz and 9 Hz), 8.20 (1H, s)

Example 2

Synthesis of
8-amino-3-chloro-N-formyl-5-thiaheptan-2-one
(process B)

A solution of 0.21 g (2.0 millimoles) of 3-chloro-3-buten-2-one in 10 mλ of ethanol was cooled to −20° C., and 0.21 g (2 millimoles) of N-forylcysteamine was added dropwise to the solution and the mixture was stirred for 30 minutes. The reaction mixture was extracted with water and chloroform, and chloroform was removed by distillation under reduced pressure to obtain 0.21 g of intended 8-amino-3-chloro-N-formyl-5-thiaheptan-2-one (the yield was 50%).

We claim:

1. An α-chloroketone derivative represented by the following general formula (I):

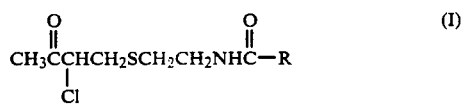

wherein R stands for a hydrogen atom, a lower alkyl group having 1 to 4 carbon atoms or an aryl group.

2. An α-chloroketone derivative as set forth in claim 1, wherein R stands for a hydrogen atom or a methyl group.

* * * * *